United States Patent [19]

Kaufman et al.

[11] Patent Number: 5,422,260

[45] Date of Patent: Jun. 6, 1995

[54] HUMAN FACTOR VIII:C MUTEINS

[75] Inventors: Randal J. Kaufman, Boston; Debra D. Pittman, Arlington, both of Mass.; John J. Toole, Palo Alto, Calif.

[73] Assignee: Genetics Institute, Inc. -Legal Affairs, Cambridge, Mass.

[21] Appl. No.: 883,936

[22] Filed: May 15, 1992

Related U.S. Application Data

[63] Continuation of Ser. No. 279,485, Dec. 2, 1988, abandoned, which is a continuation-in-part of Ser. No. 939,658, Dec. 9, 1986, which is a continuation-in-part of Ser. No. 932,767, Nov. 18, 1986, abandoned, which is a continuation-in-part of Ser. No. 868,410, May 29, 1986, abandoned.

[51] Int. Cl.$^6$ ............... C12P 21/00; C12N 15/00; C12N 1/00; A61K 37/00

[52] U.S. Cl. ............ 435/212; 435/69.1; 435/69.6; 435/69.7; 435/172.3; 435/252.3; 435/320.1; 530/383; 424/94.63; 935/10; 935/14; 935/22; 935/66

[58] Field of Search ............ 530/383, 350; 435/69.1, 435/69.6, 172.3, 252.3

[56] References Cited

U.S. PATENT DOCUMENTS

| | | | |
|---|---|---|---|
| 4,749,780 | 6/1988 | Andersson et al. | 530/383 |
| 4,757,006 | 6/1988 | Toole, Jr. et al. | 435/70 |
| 4,868,112 | 9/1989 | Toole, Jr. | 435/68 |
| 4,877,614 | 10/1989 | Andersson et al. | 424/101 |
| 4,959,318 | 9/1990 | Foster et al. | 435/69.1 |
| 4,980,456 | 12/1990 | Scondella et al. | 530/383 |
| 5,002,887 | 3/1991 | Larsen et al. | 435/212 |
| 5,004,803 | 4/1991 | Kaufman et al. | 530/383 |
| 5,045,455 | 9/1991 | Kao et al. | 435/69.6 |
| 5,112,950 | 5/1992 | Mevlien et al. | 530/383 |
| 5,171,844 | 12/1992 | Van Ooyen et al. | 530/383 |
| 5,250,421 | 10/1993 | Kaufman et al. | 435/69.6 |

FOREIGN PATENT DOCUMENTS

| | | | |
|---|---|---|---|
| 0232112 | 8/1987 | European Pat. Off. | 530/383 |
| 8606101 | 10/1986 | WIPO . | |
| 8707144 | 3/1987 | WIPO . | |

OTHER PUBLICATIONS

Eaton, D., et al., 1986, Biochemistry, 25(2):505–512.
Burke, R. L., et al., 1986, The Journal of Biological Chemistry, 261(27):12574–12578.
Bardoni, B., et al., 1988, Human Genetics 79:86–88.
Eaton, D. L., et al., 1988, in *Progress in Hemostosis and Thrombosis,* Grane and Stratton publishers, pp. 47–70.
Fass, D. N., et al., 1985, Proceedings of the National Academy of Sciences, USA, 82:1688–1691.
Foster, P. A., et al., 1988, The Journal of Biological Chemistry, 263(11):5230–5234.
Fulcher, C. A., et al., 1985, Journal of Clinical Investigation 76:117–124.
Gritschier, J., et al., 1988, Blood 72(3):1022–1028.
Kane, W. H., et al., 1988, Blood, 71(3):539–555.
Kaufman, R. H., et al., 1987, Thrombosis and Haemostasis, 58(1):537, abstract No. 1970 (Jul. 6–10, 1987, Congress).
Pittman, D. D., et al., 1987, Thrombosis and Haemostasis, 58(1):344, abstract No. 344(Jul. 6–10, 1987 Congress).
Kazazion, H. H., et al., 1986, Cold Spring Harbor Symposia on Quantitative Biology, 51:371–379.
Koedam, J. A., et al., 1987, Thrombosis and Haemostosis, 58(1):538, abstract No. 1972 (Jul. 6–10, 1987, Congress).
Rosenberg, S., et al., 1987, Thrombosis and Haemostasis, 58(1):227, abstract No. 815, (Jul. 6–10, 1987, Congress).
Langner, K. D., et al., 1988, Behring Institaten Mitt., 82:16–25.

(List continued on next page.)

*Primary Examiner*—Robert A. Wax
*Assistant Examiner*—William W. Moore
*Attorney, Agent, or Firm*—M. C. Meinert; Thomas J. DesRosier

[57] ABSTRACT

This invention relates to recombinant Factor VIII:c variants, methods to produce the variants and pharmaceutical compositions containing same.

21 Claims, 2 Drawing Sheets

Lollar, P., et al., 1988, The Journal of Biological Chemistry, 263(21): 10451–10455.

Meulien, P., et al., 1988, Protein Engineering, 2(4):301–306.

Sarver, N., et al., 1987, DNA, 6(6):553–564.

Scandella, D., et al., 1988, Proceedings of the National Academy of Sciences, USA, 85:6152–6156.

Toole, J. J., et al., 1986, Proceedings of the National Academy of Sciences, USA, 83:5939–5942.

Youssoufian, H., et al., 1988, American Journal of Human Genetics, 42: 867–871.

Wood, W. I., et al., 1984, *Nature,* 312:330–336.

Vehor, G. A., et al., 1984, Nature, 312:337–342.

Andersson, L. O., et al., 1986, Proceedings, National Academy of Sciences, USA, 83:2979–2983.

Orr, E., et al., 1985, Thrombosis and Haemostosis, 54(1): p. 54, abstract 5321.

Toole, J. J., et al., 1984, Nature, 312:342–347.

Gitschier, J., et al., 1986, Science, 232:1415–1416.

Church, W. R., et al., 1984, Proceedings of the National Academy of Sciences U.S.A. 81:6934–6937.

Eaton, D. L., et al., 1986, Biochemistry 25(26):8343–8347.

FIGURE 1A

```
MQIELSTCFF  LCLLRFCFS₁
                     A  TRRYYLGAVE  LSWDYMQSDL  GELPVDARFP  PRVPKSFPFN
                                                                    100
TSVVYKKTLF  VEFTVHLFNI  AKPRPPWMGL  LGPTIQAEVY  DTVVITLKNM  ASHPVSLHAV
                                                                    160
GVSYWKASEG  AEYDDQTSQR  EKEDDKVFPG  GSHTYVWQVL  KENGPMASDP  LCLTYSYLSH
                                                                    220
VDLVKDLNSG  LIGALLVCRE  GSLAKEKTQT  LHKFILLFAV  FDEGKSWHSE  TKNSLMQDRD
                                                                    280
AASARAWPKM  HTVNGYVNRS  LPGLIGCHRK  SVYWHVIGMG  TTPEVHSIFL  EGHTFLVRNH
                                                                    340
RQASLEISPI  TFLTAQTLLM  DLGQFLLFCH  ISSHQHDGME  AYVKVDSCPE  EPQLRMKNNE
                                                                    400
EAEDYDDDLT  DSEMDVVRFD  DDNSPSFIQI  RSVAKKHPKT  WVHYIAAEEE  DWDYAPLVLA
                                                                    460
PDDRSYKSQY  LNNGPQRIGR  KYKKVRFMAY  TDETFKTREA  IQHESGILGP  LLYGEVGDTL
                                                                    520
LIIFKNQASR  PYNIYPHGIT  DVRPLYSRRL  PKGVKHLKDF  PILPGEIFKY  KWTVTVEDGP
                                                                    580
TKSDPRCLTR  YYSSFVNMER  DLASGLIGPL  LICYKESVDQ  RGNQIMSDKR  NVILFSVFDE
                                                                    640
NRSWYLTENI  QRFLPNPAGV  QLEDPEFQAS  NIMHSINGYV  FDSLQLSVCL  HEVAYWYILS
                                                                    700
IGAQTDFLSV  FFSGYTFKHK  MVYEDTLTLF  PFSGETVFMS  MENPGLWILG  CHNSDFRNRG
                                                                    760
MTALLKVSSC  DKNTGDYYED  SYEDISAYLL  SKNNAIEPRS  FSQNSRHPST  RQKQFNATTI
                                                                    820
PENDIEKTDP  WFAHRTPMPK  IQNVSSSDLL  MLLRQSPTPH  GLSLSDLQEA  KYETFSDDPS
                                                                    880
PGAIDSNNSL  SEMTHFRPQL  HHSGDMVFTP  ESGLQLRLNE  KLGTTAATEL  KKLDFKVSST
                                                                    940
SNNLISTIPS  DNLAAGTDNT  SSLGPPSMPV  HYDSQLDTTL  FGKKSSPLTE  SGGPLSLSEE
                                                                    1000
NNDSKLLESG  LMNSQESSWG  KNVSSTESGR  LFKGKRAHGP  ALLTKDNALF  KVSISLLKTN
                                                                    1060
KTSNNSATNR  KTHIDGPSLL  IENSPSVWQN  ILESDTEFKK  VTPLIHDRML  MDKNATALRL
                                                                    1120
NHMSNKTTSS  KNMEMVQQKK  EGPIPPDAQN  PDMSFFKMLF  LPESARWIQR  THGKNSLNSG
                                                                    1180
QGPSPKQLVS  LGPEKSVEGQ  NFLSEKNKVV  VGKGEFTKDV  GLKEMVFPSS  RNLFLTNLDN
                                                                    1240
LHENNTHNQE  KKIQEEIEKK  ETLIQENVVL  PQIHTVTGTK  NFMKNLFLLS  TRQNVEGSYE
                                                                    1300
GAYAPVLQDF  RSLNDSTNRT  KKHTAHFSKK  GEEENLEGLG  NQTKQIVEKY  ACTTRISPNT
                                                                    1360
SQQNFVTQRS  KRALKQFRLP  LEETELEKRI  IVDDTSTQWS  KNMKHLTPST  LTQIDYNEKE
                                                                    1420
KGAITQSPLS  DCLTRSHSIP  QANRSPLPIA  KVSSFPSIRP  IYLTRVLFQD  NSSHLPAASY
                                                                    1480
RKKDSGVQES  SHFLQGAKKN  NLSLAILTLE  MTGDQREVGS  LGTSATNSVT  YKKVENTVLP
                                                                    1540
KPDLPKTSGK  VELLPKVHIY  QKDLFPTETS  NGSPGHLDLV  EGSLLQGTEG  AIKWNEANRP
                                                                    1600
GKVPFLRVAT  ESSAKTPSKL  LDPLAWDNHY  GTQIPKEEWK  SQEKSPEKTA  FKKKDTILSL
                                                                    1660
NACESNHAIA  AINEGQNKPE  IEVTWAKQGR  TERLCSQNPP  VLKRHQREIT  RTTLQSDQEE
                                                        (continued --->)
```

FIGURE 1B

```
                                                                    1720
IDYDDTISVE  MKKEDFDIYD  EDENQSPRSF  QKKTRHYFIA  AVERLWDYGM  SSSPHVLRNR
                                                                    1780
AQSGSVPQFK  KVVFQEFTDG  SFTQPLYRGE  LNEHLGLLGP  YIRAEVEDNI  MVTFRNQASR
                                                                    1840
PYSFYSSLIS  YEEDQRQGAE  PRKNFVKPNE  TKTYFWKVQH  HMAPTKDEFD  CKAWAYFSDV
                                                                    1900
DLEKDVHSGL  IGPLLVCHTN  TLNPAHGRQV  TVQEFALFFT  IFDETKSWYF  TENMERNCRA
                                                                    1960
PCNIQMEDPT  FKENYRFHAI  NGYIMDTLPG  LVMAQDQRIR  WYLLSMGSNE  NIHSIHFSGH
                                                                    2020
VFTVRKKEEY  KMALYNLYPG  VFETVEMLPS  KAGIWRVECL  IGEHLHAGMS  TLFLVYSNKC
                                                                    2080
QTPLGMASGH  IRDFQITASG  QYGQWAPKLA  RLHYSGSINA  WSTKEPFSWI  KVDLLAPMII
                                                                    2140
HGIKTQGARQ  KFSSLYISQF  IIMYSLDGKK  WQTYRGNSTG  TLMVFFGNVD  SSGIKHNIFN
                                                                    2200
PPIIARYIRL  HPTHYSIRST  LRMELMGCDL  NSCSMPLGME  SKAISDAQIT  ASSYFTNMFA
                                                                    2260
TWSPSKARLH  LQGRSNAWRP  QVNNPKEWLQ  VDFQKTMKVT  GVTTQGVKSL  LTSMYVKEFL
                                                                    2320
ISSSQDGHQW  TLFFQNGKVK  VFQGNQDSFT  PVVNSLDPPL  LTRYLRIHPQ  SWVHQIALRM

EVLGCEAQDL  Y
```

HUMAN FACTOR VIII:C MUTEINS

Certain aspects of the research resulting in the present invention were funded in part by the U.S. Department of Health and Human Services (DHHS) under a Small Business Innovation Research (SBIR) Grant, DHSS Grant No. 1 R43 HL35946-01. The United States Government has certain rights in aspects of this invention.

CROSS-REFERENCE TO RELATED APPLICATIONS

This application is a continuation of U.S. Ser. No. 07/279,485 (filed Dec. 2, 1988 and abandoned May 15, 1992), which is a continuation-in-part application of U.S. Ser. No. 06/939,658 (filed Dec. 9, 1986), which is a continuation-in-part of U.S. Ser. No. 06/932,767 (filed Nov. 18, 1986 and abandoned Jul. 15, 1988), which is a continuation-in-part of U.S. Ser. No. 06/868,410 (filed May 29, 1986 and abandoned Jul. 15, 1988).

Indirectly related patent applications include the series directed to Factor VIII: U.S. Ser. No. 07/386,280 (filed Jul. 28, 1989), now abandoned, which is a continuation-in-part of U.S. Ser. No. 07/136,478 (filed Dec. 23, 1987 and abandoned May 22, 1990), which is a file wrapper continuation of U.S. Ser. No. 06/644,036 (filed Aug. 24, 1984 and abandoned Dec. 23, 1987), which is a continuation-in-part of U.S. Ser. No. 06/546,650 (filed Oct. 28, 1983 and issued as U.S. Pat. No. 4,757,006 on Jul. 12, 1988).

Another series of indirectly related patent applications directed to Factor VIII B domain deletions are: U.S. Ser. No. 07/409,191 (filed Sep. 19, 1989 and abandoned Feb. 25, 1992), which is a continuation-in-part of U.S. Ser. No. 07/010,085 (filed Apr. 11, 1986 and issued Sep. 19, 1989 as U.S. Pat. No. 4,868,112), which is a continuation-in-part of U.S. Ser. No. 06/725,350 (filed Apr. 12, 1985 and abandoned Mar. 4, 1987).

Yet another series of indirectly related applications disclosing Factor VIII co-expression with vWF and/or phospholipid are: U.S. Ser. No. 07/824,765 (filed Jan. 17, 1992 and issued as U.S. Pat. No. 5,250,421), which is a file wrapper continuation of U.S. Ser. No. 07/260,085 (filed Oct. 14, 1988), now abandoned, which is a continuation of U.S. Ser. No. 07/068,865 (filed Jul. 2, 1987 and abandoned Sep. 8, 1989), which is a continuation-in-part of U.S. Ser. No. 07/034,882 (filed Apr. 6, 1987 and abandoned Sep. 8, 1989), which is a continuation-in-part of U.S. Ser. No. 06/942,338 (filed Dec. 16, 1986 and abandoned Aug. 22, 1991), which is a continuation-in-part of U.S. Ser. No. 06/816,031 (filed Jan. 3, 1986 and abandoned Jan. 23, 1989).

The contents of these applications are hereby incorporated by reference, as are the contents of International Application WO87/07144 (published Dec. 3, 1987) related to cleavage site mutants.

This invention relates to substances having procoagulant activity. More specifically, this invention relates to "recombinant" procoagulant proteins, a process for obtaining the proteins from genetically engineered cells, and therapeutic compositions containing the proteins for use as procoagulant agents.

The characterization of human factor VIII from plasma indicates that its coagulant activity is associated with a multitude of polypeptide chains having molecular weights ranging from about 50,000 to about 210,000 daltons. Upon addition of thrombin, there is a specified pattern of proteolysis which initially activates and then inactivates the factor VIII procoagulant activity. Definition of the proteolytic cleavages necessary for factor VIII activation and inactivation is required in order to understand the structural requirements for factor VIII activity. One approach has been that of protein sequencing of specific cleavage products before and after digestion with thrombin (Eaton et al., 1986, Biochem. 25:505; Smart et al., 1986, PNAS USA 83:2979-2983). This approach has been somewhat useful in mapping locations of certain proteolytic sites for this protease along the factor VIII molecule.

We have now analyzed human recombinant factor VIII derived from a mammalian host cell system and elucidated the same cleavage sites as determined from plasma derived VIII. Our data suggest that the recombinant protein and the natural protein are folded and processed similarly, a result which could not be predicted with confidence a priori. Our data was obtained using recombinant factor VIII purified from conditioned medium from a mammalian cell line which was engineered to produce factor VIII. The recombinant protein so obtained was characterized as a complex of an approximately 200 kD polypeptide and an approximately 80 kD polypeptide. Upon digestion with thrombin, the 200 kD species yields an approximately 90 kD species with eventual generation of an approximately 54 and a 44 kD species. Upon thrombin digestion the 80 kD species is cleaved to an approximatley 73 kD form. The 80 kD and 73 kD species are also referred to elsewhere as the "76 kD" and "69 kD" species using the nomenclature of porcine FVIII. Despite the awareness of various species of FVIII fragments, the knowledge of the existence of precise cleavage sites has not heretofore definitively established what cleavages are respectively necessary for activation and for subsequent inactivation.

BRIEF DESCRIPTION OF THE DRAWINGS

FIGS. 1A and 1B collectively depict the amino acid sequence of the human Factor VIII:c wherein the amino terminus of the mature protein is Ala at position 1.

In a further aspect of the research resulting in the present invention, the approach of site-specific mutagenesis coupled with expression of the altered forms of the factor VIII DNA was used to elucidate what sites are necessary and sufficient for the activation, as well as for inactivation of the factor VIII molecule. Specific DNA sequences were changed in order to alter specific amino acids which result in the inactivation of specific cleavage sites. The modified forms of factor VIII were produced using cloned, modified factor VIII-encoding cDNAs in a mammalian host cell system capable of high level expression (Kaufman, PNAS, 1985, 82:689). The modified forms of FVIII so produced were then analyzed. Our results indicated that a mutation that results in protein that is not cleaved at the 90 kD cleavage site or 80 kD cleavage site does not reduce procoagulant activity or thrombin activatability. The predominant species generated in the conditioned medium from the 80 kD cleavage site mutation, at least in the case of deletion variants described hereinafter, is a single chain as monitored by SDS-polyacrylamide gel electrophoresis. Mutation of the thrombin cleavage site otherwise generating the 54 and 44 kD species renders factor VIII inactive. Mutation of the proposed activated protein C ("APC") cleavage site at the amino terminus renders factor VIII which has increased specific activity and perhaps decreased susceptibility to proteolytic inactivation. Experimental evidence suggests that APC catalyzes proteolytic cleavage immediately "downstream" of Arg-336 (i.e. between Arg-336 and Met-337) and if cleavage at that site is blocked as described below, perhaps immediately downstream of one or more of Lys-325, Lys-338, and Arg-359.

This invention provides a family of Factor VIII:c proteins containing modifications relative to natural human Factor VIII:c which reduce the lability of the molecules for specific protease-catalyzed cleavage at one or more of the cleavage sites of natural human Factor VIII:c but which retain procoagulant activity and thrombin activatibility. The sites susceptible to modification in accord with this invention are referred to hereinafter simply as "cleavage sites" and include the cleavage site between Arg-226 and Ala-227, the "APC" cleavage site including the site between Arg-336 and Met-337 and/or the other proposed "APC" cleavage sites mentioned in the preceding paragraph, the cleavage site between Arg-562 and Gly-563, the "90 kD cleavage site" between Arg-740 and Ser-741, the "95 kD cleavage site" between Arg-776 and Thr-777, the "115 kD cleavage site" between Arg-1313 and Ala-1314, the "76 kD cleavage site" between Arg-1648 and Glu-1649, and the "Factor Xa cleavage site" between Arg-1721 and Ala-1722, as well as Arg-698 and Arg-700. Throughout this disclosure the numbering of amino acids is with reference to the amino acid sequence of Factor VIII:c as depicted in Table 1, wherein the amino terminus of the mature protein is Ala-1.

By "Factor VIII:c proteins" (also referred to hereinafter as "variants"), we mean proteins exhibiting factor VIII procoagulant activity (i.e. as measured by conventional FVIII clotting assays) which are characterized by an amino acid sequence the same or substantially the same, except at one or more cleavage sites, as the amino acid sequence of natural human Factor VIII:c or of analogs thereof (hereinafter, "deletion analogs") containing deletions of one or more amino acids between Ser-373 and Arg-1689, inclusive, which retain procoagulant activity. By an amino acid sequence "substantially the same" as that of natural human factor VIII:c except at one or more cleavage sites we contemplate all factor VIII proteins which are characterized by (i) amino acid modification at one or more sites identified herein and (ii) either (a) being encoded by a DNA capable of hybridizing under stringent conditions to a DNA which encodes natural human fVIII:c or (b) having a mature N-terminal peptide sequence the same or substantially the same as the first 40 amino acids and a C-terminal peptide sequence the same or substantially the same as the last 50 amino acids shown in Table I. Thus, factor VIII proteins include full-length and deletion analogs with one or more cleavage site modifications, as described herein, with or without further modification(s), so long as the proteins are active procoagulant or coagulant proteins and either (i) are encoded by a cDNA capable of hybridizing under stringent conditions [e.g., under conditions equivalent to 65° C. in 5×SSC (1×SSC=150 mM NaCl/0.15M Na citrate)] to a cDNA which encodes a natural human factor VIII:c or (ii) have the same or substantially the same 40 amino acid mature N-terminus and 50 amino acid C-terminus as that shown in Table I. Exemplary other modifications encompassed by this invention include but are not limited to modifications embodied by "sulfation mutants", i.e. factor VIII:c proteins characterized by amino acid substitution for or deletion of tyrosine at one or more potential sulfation sites, e.g. at positions 346, 395, 407, 718, 719, 723, 1664, 1680 and 1709, with or without the previously mentioned modifications.

The modified forms of factor VIII of this invention may be capable of production in more homogeneous and/or more stable form than plasma-derived or unmodified recombinant factor VIII and may have beneficial effects upon administration in vivo resulting from increased activity of a single chain molecule, decreased inactivation due to protein C inactivation, increased half-life or specific activity, and/or improved pharmacokinetic profile. These proteins may thus permit decreased dosages and/or alternative routes of administration relative to unmodified Factor VIII:c.

One aspect of the invention relates to variants wherein one or more of the Factor Xa, APC and thrombin cleavage sites are modified to render such sites less labile to specific proteolysis, for example, wherein one or both of the amino acids defining the cleavage site, preferably at least the arginine residue, is deleted or, as is preferred at present, replaced by a different amino acid. The replacement may be a conservative change, e.g. the replacement of Arg with Lys, to minimize the chance of effecting a change in the secondary structure of the protein. Alternatively the change may be a non-conservative change, e.g. the replacement of Arg with a non-basic amino acid such as Ile, to better assure resistance to proteolysis. Furthermore, the replacement of a cleavage site amino acid may be with more than one amino acid. For example, an Arg may be replaced with a single amino acid, a dipeptide or a tripeptide such as Ile, Ile-Leu, Leu-Ile, Ile-Leu-Gly, etc. Compounds of this aspect of the invention thus include variants wherein Arg at one or more of positions 220, 226, 250, 279, 282, 336, 359, 562, 698. 700, 740 (and/or Ser-741), 776, 1313, 1648, 1719 and 1721, is deleted or replaced by one or more amino acids, independently selected from lysine or a non-basic amino acid such as isoleucine, for example. This invention further encompasses Factor VIII:c proteins which contain Lys substituted for Arg-1689 at the 73 kD cleavage site, alone or in combination with other modifications described herein. Furthermore, one or both of lys-325 and lys-338 may be deleted or replaced, e.g. with a non-basic amino acid.

Another aspect of the invention relates to variants wherein (a) a tripeptide sequence spanning one or more of the cleavage sites and/or (b) any one or more of the above-mentioned amino acids which may be modified in accordance with this invention is replaced by a consensus asparagine-linked glycosylation site. Consensus N-linked glycosylation sites comprise tripeptide sequences of the formula asparagine-X-threonine or asparagine-X-serine, where X is generally any amino acid except perhaps proline. Exemplary compounds of this aspect of the invention include variants in which the sequence "NRA" spanning the Factor Xa cleavage site is replaced with "NRS" or "NRT". Compounds of this aspect of the invention containing an engineered N-linked glycosylation site at one or more cleavage sites may additionally contain a modification such as arginine and/or lysine deletion or replacement at one or more other cleavage sites, and/or deletion or replacement of tyrosine at one or more sulfation sites, in accordance with the previously-described aspect of the invention. An exemplary compound of this sort contains an Ile substituted for Arg at position 1648 in the 80 kD cleavage site and the sequence NRS or NRT substituted for NRA at the Factor Xa cleavage site (positions 1720-1722).

One subgenus of variants of particular interest at present includes those containing a modification at the 80 kD cleavage site. These variants thus contain a point deletion or preferably an amino acid substitution at Arg-1648 or a consensus N-linked glycosylation site comprising the sequence -NXT- or -NXS- (wherein X is any amino acid, preferably not proline, however) substituted for Arg-1648, or for QRE, or preferably HQR or REI, the three tripeptide sequences spanning the 80 kD cleavage site. This subgenus includes variants modified only at the 80 kD site, and in addition, e.g. at one, two, three, four, five,

TABLE I

Full-length Protein Sequence of Human Factor VIII:c

MQIELSTCFF LCLLRFCFS
1

A TRRYYLGAV LSWDYMQSDL GELPVDARFP PRVPKSFPFN
100

TSVVYKKTLF VEFTDHLFNI AKPRPPWMGL LGPTIQAEVY DTVVITLKNM ASHPVSLHAV
160

GVSYWKASEG AEYDDQTSQR EKEDDKVFPG GSHTYVWQVL KENGPMASDP LCLTYSYLSH
220

VDLVKDLNSG LIGALLVCRE GSLAKEKTQT LHKFILLFAV FDEGKSWHSE TKNSLMQDRD
280

AASARAWPKM HTVNGYVNRS LPGLIGCHRK SVYWHVIGMG TTPEVHSIFL EGHTFLVRNH
340

RQASLEISPI TFLTAQTLLM DLGQFLLFCH ISSHQHDGME AYVKVDSCPE EPQLRMKNNE
400

EAEDYDDDLT DSEMDVVRFD DDNSPSFIQI RSVAKKHPKT WVHYIAAEEE DWDYAPLVLA
PDDRSYKSQY LNNGPQRIGR KYKKVRFMAY TDETFKTREA IQHESGILGP LLYGEVGDTL
520

LIIFKNQASR PYNIYPHGIT DVRPLYSRRL PKGVKHLKDF PILPGEIFKY KWTVTVEDGP
580

TKSDPRCLTR YYSSFVNMER DLASGLIGPL LICYKESVDQ RGNQIMSDKR NVILFSVFDE
640

NRSWYLTENI QRFLPNPAGV QLEDPEFQAS NIMHSINGYV FDSLQLSVCL HEVAYWYILS
700

IGAQTDFLSV FFSGYTFKHK MVYEDTLTLF PFSGETVFMS MENPGLWILG CHNSDFRNRG
760

MTALLKVSSC DKNTGDYYED SYEDISAYLL SKNNAIEPRS FSQNSRHPST RQKQFNATTI
820

PENDIEKTDP WFAHRTPMPK IQNVSSSDLL MLLRQSPTPH GLSLSDLQEA KYETFSDDPS
880

PGAIDSNNSL SEMTHFRPQL HHSGDMVFTP ESGLQLRLNE KLGTTAATEL KKLDFKVSST
940

SNNLISTIPS DNLAAGTDNT SSLGPPSMPV HYDSQLDTTL FGKKSSPLTE SGGPLSLSEE
1000

NNDSKLLESG LMNSQESSWG KNVSSTESGR LFKGKRAHGP ALLTKDNALF KVSISLLKTN
1060

KTSNNSATNR KTHIDGPSLL IENSPSVWQN ILESDTEFKK VTPLIHDRML MDKNATALRL
1120

NHMSNKTTSS KNMEMVQQKK EGPIPPDAQN PDMSFFKMLF LPESARWIQR THGKNSLNSG
1180

QGPSPKQLVS LGPEKSVEGQ NFLSEKNKVV VGKGEFTKDV GLKEMVFPSS RNLFLTNLDN
1240

LHENNTHNQE KKIQEEIEKK ETLIQENVVL PQIHTVTGTK NFMKNLFLLS TRQNVEGSYE
1300

GAYAPVLQDF RSLNDSTNRT KKHTAHFSKK GEEENLEGLG NQTKQIVEKY ACTTRISPNT
1360

SQQNFVTQRS KRALKQFRLP LEETELEKRI IVDDTSTQWS KNMKHLTPST LTQIDYNEKE
1420

KGAITQSPLS DCLTRSHSIP QANRSPLPIA KVSSFPSIRP IYLTRVLFQD NSSHLPAASY
1480

RKKDSGVQES SHFLQGAKKN NLSLAILTLE MTGDQREVGS LGTSATNSVT YKKVENTVLP
1540

TABLE I-continued
Full-length Protein Sequence of Human Factor VIII:c

```
KPDLPKTSGK VELLPKVHIY QKDLEPTETS NGSPGHLDLV EGSLLQGTEG AIKWNEANRP
                                                                  1600

GKVPFLRVAT ESSAKTPSKL LDPLSWDNHY GTQIPKEEWK SQEKSPEKTA FKKKDTILSL
                                                                  1660

NACESNHAIA AINEGQNKPE IEVTWAKQGR TERLCSQNPP VLKRHQRETT RTTLQSDQEE
                                                                  1720

IDYDDTISVE MKKEDFDIYD EDENQSPRSF QKKTRHYFIA AVERLWDYGM SSSPHVLRNR
                                                                  1780

AQSGSVPQFK KVVFQEFTDG SFTQPLYRGE LNEHLGLLGP YIRAEVEDNI MVTFRNQASR
                                                                  1840

PYSFYSSLIS YEEDQRQGAE PRKNFVKPNE TKTYFWKVQH HMAPTKDEFD CKAWAYFSDV
                                                                  1900

DLEKDVHSGL IGPLLVCHTN TLNPAHGRQV TVQEFALFFT IFDETKSWYF TENMERNCRA
                                                                  1960

PCNIQMEDPT FKENYRFHAI NGYIMDTLPG LVMAQDQRIR WYLLSMGSNE NIHSIHFSGH
                                                                  2020

VFTVRKKEEY KMALYNLYPG VFETVEMLPS KAGIWRVECL IGEHLHAGMS TLFLVYSNKC
                                                                  2080

QTPLGMASGH IRDFQITASG QYGQWAPKLA RLHYSGSINA WSTKEPFSWI KVDLLAPMII
                                                                  2140

HGIKTQGARQ KFSSLYISQF IIMYSLDGKK WQTYRGNSTG TLMVFFGNVD SSGIKHNIFN
                                                                  2200

PPIIARYIRL HPTHYSIRST LRMELMGCDL NSCSMPLGME SKAISDAQIT ASSYFTNMFA
                                                                  2260

TWSPSKARLH LQGRSNAWRP QVNNPKEWLQ VDFQKTMKVT GVTTQGVKSL LTSMYVKEFL
                                                                  2320

ISSSQDGHQW TLFFQNGKVK VFQGNQDSFT PVVNSLDPPL LTRYLRIHPQ SWVHQIALRM
EVLGCEAQDL Y
``` six or more other sites within the purview of this invention and optionally containing Lys instead of Arg at position 1689. For example, this subgenus includes variants in which Arg-1648 is deleted or is replaced with another amino acid or Glu-1649 is deleted or is replaced with Asn, which variants further contain a replacement amino acid for Arg-1313. This subgenus also includes variants modified at one or more of the proposed APC, 90 kD, 95 kD 115 kD, 80 kD, 73 kD (lysine substitution only) and Xa cleavage sites.

Also, of particular interest at present is the subgenus of variants containing modification at both the proposed APC and Xa cleavage sites. This subgenus also includes variants modified at one or more of the other cleavage sites, including preferably the 80 kD site. Exemplary variants of particular interest at present are depicted in the Table below. Positions marked "X" in the Table indicate the site of deletion of an amino acid or replacement thereof with independently selected replacement amino acids. By "independently selected" we mean that where more than one amino acid position is modified ("X" in the following Table), replacement amino acids for the respective positions may be the same or different from each other, and one or more of the sites may be modified by deletion while one or more of the other sites may be modified by amino acid substitution. Thus in Compound 19 of the Table below, Arg-740 may be replaced with Ile and Arg-1648 may be replaced with Leu, for example. Alternatively, Arg-740 may be deleted and Arg-1648 replaced with Ile.

Variants in accordance with this invention also include proteins modified as described herein which additionally contain allelic variations, i.e. variations in sequence due to natural variability from individual to individual, or other amino acid substitutions or deletions, so long as such variants still retain FVIII procoagulant activity.

All variants of this invention may be prepared by expressing recombinant DNAs encoding the desired variant in host cells, preferably mammalian host cells, as is known in the art. DNA sequences encoding the variants may be produced by conventional site-directed mutagenesis of DNA sequences encoding human FVIII:c or the deletion analogs thereof.

DNA sequences encoding human Factor VIII:c have been cloned. One sequence encoding the full-length human protein of Table I as well as a sequence encoding the deletion analog pDGR-2 (ATCC No. 53100) have been deposited with the American Type Culture Collection (Rockville, Md.).

Preparation and nucleotide sequence of the full-length human factor VIII:c cDNA has been set forth in detail in U.S. Pat. No. 4,757,006 and in International Patent Application No. PCT/US84/01641, published May 9, 1985 (Publn. No. WO 85/01961). A pSP64 recombinant clone containing the nucleotide sequence depicted in Table I, designated as pSP64-VIII, is on deposit at the ATCC under Accession Number ATCC 39812.

To prepare cDNA encoding deletion analogs of Factor VIII:c, restriction endonucleases were used to obtain cleavage of the full-length human factor VIII:c cDNA, at appropriate sites in the nucleotide sequence. Restriction endonucleases are generally utilized under the conditions and in the manner recommended by their commercial suppliers. The restriction endonucleases selected are those which will enable one to excise with substantial specificity sequences that code for the portion of the factor VIII:c molecule desired to be excised. BamHI and SacI are particularly useful endonucleases. However, the skilled artisan will be able to utilize other restriction endonucleases chosen by conventional selection methods. The number of nucleotides

TABLE II

Exemplary Variants of this Invention
Factor VIII: C proteins* characterized by:
Deletion or substitution** of:

| Compound | APC Arg 336 | APC Lys 325 | APC Lys 338 | APC Arg 359 | 90 kD Arg 740 | 80 kD Arg 1648 | Xa R &/or R 1721 1719 |
|---|---|---|---|---|---|---|---|
| 1 | X | | | | | | |
| 2 | X | X | | | | | |
| 3 | X | | X | | | | |
| 4 | X | | | X | | | |
| 5 | X | X | X | | | | |
| 6 | X | X | | X | | | |
| 7 | X | | X | X | | | |
| 8 | X | X | X | X | | | |
| 9 | | | | | X | | |
| 10 | X | | | | X | | |
| 11 | X | X | | | X | | |
| 12 | X | | X | | X | | |
| 13 | X | | | X | X | | |
| 14 | X | X | X | | X | | |
| 15 | X | X | | X | X | | |
| 16 | X | | X | X | X | | |
| 17 | X | X | X | X | X | | |
| 18 | | | | | | X | |
| 19 | | | | | X | X | |
| 20 | X | | | | | X | |
| 21 | X | X | | | | X | |
| 22 | X | | X | | | X | |
| 23 | X | | | X | | X | |
| 24 | X | X | X | | | X | |
| 25 | X | X | | X | | X | |
| 26 | X | | X | X | | X | |
| 27 | X | X | X | X | | X | |
| 28 | X | | | | X | X | |
| 29 | X | X | | | X | X | |
| 30 | X | | X | | X | X | |
| 31 | X | | | X | X | X | |
| 32 | X | X | X | | X | X | |
| 33 | X | X | | X | X | X | |
| 34 | X | | X | X | X | X | |
| 35 | X | X | X | X | X | X | |
| 36 | | | | | | | X |
| 37 | X | | | | | | X |
| 38 | X | X | | | | | X |
| 39 | X | | X | | | | X |
| 40 | X | | | X | | | X |
| 41 | X | X | X | | | | X |
| 42 | X | X | | X | | | X |
| 43 | X | | X | X | | | X |
| 44 | X | X | X | X | | | X |
| 45 | | | | | X | | X |
| 46 | X | | | | X | | X |
| 47 | X | X | | | X | | X |
| 48 | X | | X | | X | | X |
| 49 | X | | | X | X | | X |
| 50 | X | X | X | | X | | X |
| 51 | X | X | | X | X | | X |
| 52 | X | | X | X | X | | X |
| 53 | X | X | X | X | | X | X |
| 54 | | | | | | X | X |
| 55 | | | | | X | X | X |
| 56 | X | | | | | X | X |
| 57 | X | X | | | | X | X |
| 58 | X | | X | | | X | X |
| 59 | X | | | X | | X | X |
| 60 | X | X | X | | | X | X |
| 61 | X | X | | X | | X | X |
| 62 | X | | X | X | | X | X |
| 63 | X | X | X | X | | X | X |
| 64 | X | | | | X | X | X |
| 65 | X | X | | | X | X | X |
| 66 | X | | X | | X | X | X |
| 67 | X | | | X | X | X | X |
| 68 | X | X | X | | X | X | X |
| 69 | X | X | | X | X | X | X |
| 70 | X | | X | X | X | X | X |
| 71 | X | X | X | X | X | X | X |

*Factor VIII: C proteins including full-length FVIII and deletion analogs, including those wherein:
a. A-982 through L-1562 is deleted ("DGR")
b. S-741 through R-1648 is deleted (90-80kD, "DB")
c. S-741 through Q-1647 is deleted (90-R-80kD, "DBR")
d. S-373 through R-1648 is deleted (54-80kD)
e. T-670 through P-1640 is deleted ("LA")
**The amino acid indicated is either deleted or replaced by a different amino acid, e.g. R → I or K; K → I, for example.

deleted may vary but care should be taken to insure that the reading frame of the ultimate cDNA sequence will not be affected.

The DNA sequences encoding the deletion analogs can, in addition to other methods, be derived from the full-length sequence of human factor VIII:c DNA by application of oligonucleotide-mediated deletion mutagenesis, referred to also as "loopout" mutagenesis, as described for example in Morinaga, Y. et al. *Biotechnology*, 2:636–639 (1984).

Deletion analogs containing a deletion of 1–951 amino acids between the 90 kD and 73 kD cleavage sites and methods for their preparation are described in detail in International Application No. PCT/US86/00774 (published 23 Oct. 1986 as WO 86/06101), based thereon. Plasmid pDGR-2 which contains cDNA encoding a deletion analog lacking 581 amino acids has been deposited with the American Type Culture Collection as ATCC 53100. Analogous deletion variants containing a deletion of one or more amino acids between Arg-372 (at the 54/44 cleavage site) and Set-1690 (at the 73kD cleavage site) can be prepared using the general methods described in PCT/US86/00774, supra. More specifically, a DNA molecule encoding such deletion analogs may be readily prepared from a DNA molecule encoding either full-length Factor VIII or a previous deletion analog such as pDGR-2, by loop-out mutagenesis using appropriate oligonucleotides or by excision of regions to be deleted using appropriate restriction enzymes, as will be readily understood by those of ordinary skill in this art.

By these means one may readily prepare a cDNA encoding a protein having fVIII:c procoagulant activity wherein the protein is characterized by amino acid sequence:

In the formula A-X-B, A represents a protein region comprising the polypeptide sequence Ala-1 through Arg-372 of a full-length sequence of factor VIII:c, e.g. substantially as shown in Table I. B represents a protein region comprising the polypeptide sequence Ser-1690 through Tyr-2332 of a full-length sequence of Factor VIII:c, e.g. substantially as shown in Table I. X represents a protein region comprising 0–1316 amino acids substantially duplicative of sequences of amino acids within the sequence Arg-372 through Ser-1690 of a full-length sequence of Factor VIII:c, e.g. substantially as shown in Table I. It should be understood that the amino terminus of X is covalently bonded through a peptide bond to the carboxy terminus of A, and the carboxyl terminus of X is likewise bonded to the amino terminus of B. It should be further understood, however, that where X represents 0 amino acids, the amino terminus of A is covalently bonded by a peptide bond directly to the carboxyl terminus of B, to form an Arg-372:Ser-1690 fusion. Proteins of this invention may be produced by culturing a host cell containing the appropriate cDNA using conventional expression vectors and techniques. Proteins of this invention include, inter alia, proteins of the formula A-X-B wherein X comprises a peptide sequence of 0-367 amino acids substantially duplicative of sequences of amino acids within the sequence Arg-372 through Arg-740 of a full-length sequence of factor VIII:c, e.g., substantially as shown in Table I. Presently preferred variants contain deletions as specified in the second following sentence.

Variants of this invention which embody both modification at one or more of cleavage sites and internal deletion relative to the native FVIII molecule, preferably contain an internal deletion between the 90 kD and 80 kD cleavage sites. Exemplary such deletions include (i) a deletion of A-982 through L-1562 ("DGR"); (ii) a deletion of S-741 through R-1648 (fusing R-740 of the 90 kD site to E-1649 of the 80 kD site); (iii) a deletion of S-741 through Q-1647 (fusing R-740 of the 90 kD site to R-1648 of the 80 kD site); or (iv) deletions of fewer amino acids within the regions specified in (i)–(iii). Other variants of this invention embodying both modification at one or more cleavage sites and internal deletion may contain deletion of one or more amino acids between the 54/44 kD cleavage site spanning R-372 and the 80 kD site cleavage site spanning R-1648 or between the 90 kD site spanning R-740 and the 73 kD site spanning R-1689.

As mentioned above, DNA sequences encoding individual variants of this invention may be produced by conventional site-directed mutagenesis of a DNA sequence encoding human Factor VIII:C or deletion analogs thereof. Such methods of mutagenesis include the M13 system of Zoller and Smith, Nucleic Acids Res. 10:6487–6500 (1982); Methods Enzymol. 100:468–500 (1983); and DNA 3:479–488 (1984), using single stranded DNA and the method of Morinaga et al., Bio/technology, 636–639 (July 1984), using heteroduplexed DNA. Exemplary oligonucleotides used in accordance with such methods to convert an arginine codon to a codon for isoleucine, for example, are shown in Table III. It should be understood, of course, that DNA encoding each of the proteins of this invention may be analogously produced by one skilled in the art through site-directed mutagenesis using appropriately chosen oligonucleotides.

The new DNA sequences encoding these variants can be introduced into appropriate vectors operably linked to an expression control sequence, i.e. containing a promoter and optionally other elements such as an an enhancer, capable of directing expression in mammalian cells. The procoagulant activity produced by the host cells transiently transfected or stably transformed with such expression vectors, or the progeny of such cells, may be measured by using standard assays for blood plasma samples. Preferably the host cells expressing the FVIII variant also coproduce vWF protein, as described in WO 87/04187.

Furthermore, in embodiments wherein the 80 kD cleavage site is not modified to prevent cleavage, the desired protein may be produced by separate expression of the 5' portion of the DNA which encodes the heavy chain and the 3' portion of the DNA which encodes the light chain, although this embodiment is not presently preferred. Naturally, termination and polyadenylation signals must be provided for the 5' DNA portion and an expression control sequence and leader sequence must be provided for the 3' DNA portion when they are separately expressed. When the two portions of the protein are separately expressed, they may be separately expressed in the same host cells or in separate host cells. Separate protein subunits may be assembled by methods now known in the art or by the method of U.S. Ser. No. 190,276 (filed May 4, 1988).

Throughout this disclosure it should be appreciated that the following well known 3- and 1-letter codes are used:

| amino acid | 3 | 1 | amino acid | 3 | 1 |
|---|---|---|---|---|---|
| alanine | ala | A | tyrosine | tyr | Y |
| valine | val | V | asparagine | asp | N |
| leucine | leu | L | glutamine | gln | Q |
| isoleucine | ile | I | aspartic acid | asp | D |
| proline | pro | P | glutamic acid | glu | E |
| phenylalanine | phe | F | lysine | lys | K |
| tryptophan | trp | W | arginine | arg | R |
| methionine | met | M | histidine | his | H |
| glycine | gly | G | cysteine | cys | C |
| serine | ser | S | | | |
| threonine | thr | T | | | |

TABLE III

Exemplary Oligonucleotides

| No. | Sequence | Mutation |
|---|---|---|
| 1. | GTC TTG AAA CGC CAT CAA ATA GAA ATA ACT CGT ACT ACT | $R_{1648} \longrightarrow I$ |
| 2. | CAT CAA ATA GAA ATA | *(1) |
| 3. | CGC CAT CAA CGG AAC ATA ACT CGT ACT ACT | $E_{1649} \longrightarrow N$ |
| 4. | CAS CGG AAC ATA AC | *(3) |
| 5. | GCC ATT GAA CCA ATC AGC TTC TCC CAG | $R_{740} \longrightarrow I$ |
| 6. | GAA CCA ATC AGC TTC | *(5) |

TABLE III-continued

Exemplary Oligonucleotides

| No. | Sequence | Mutation |
|---|---|---|
| 7. | C TTT ATC CAA ATT <u>ATC</u> TCA GTT GCC AAG | $R_{372} \longrightarrow I$ |
| 8. | CAA ATT ATC TCA GTT | *(7) |
| 9. | GT CCA GAG GAA CCC CAA CTA <u>AAG</u> ATG AAA AAT AAT GAA GCGG | $R_{336} \longrightarrow K$ |
| 10. | CAA CTA AAG ATG AAA | *(9) |
| 11. | GAA AAT CAG AGC CCC <u>AAA</u> AGC TTT CAA AAG AAA AC | $R_{1689} \longrightarrow K$ |
| 12. | AGC CCC AAA AGC TTT | *(11) |
| 13. | CAA CGT AGT AAG <u>ATC</u> GCT TTG AAA CAA TTC | $R_{1313} \longrightarrow I$ |
| 14. | AGT AAG ATC GCT TTG | *(13) |

*Used for screening mutagenesis event effected with the oligonucleotide indicated in parentheses. Codons for replacement amino acids are underlined. As those skilled in this art will appreciate, oligonucleotides can be readily constructed for use in deleting one or more amino acids or for inserting a different (replacement) amino acid at a desired site by deleting one or more codons or substituting the codon for the desired amino acid in the oligonucleotide, respectively. Other mutagenesis oligonucleotides can be designed based on an approximately 20–50 nucleotide sequence spanning the desired site, with replacement or deletion of the original codon(s) one wishes to change.

The eukaryotic cell expression vectors described herein may be synthesized by techniques well known to those skilled in this art. The components of the vectors such as the bacterial replicons, selection genes, enhancers, promoters, and the like may be obtained from natural sources or synthesized by known procedures. See Kaufman et al., *J. Mol. Biol.*, 159:601–621 (1982); Kaufman, *Proc. Natl. Acad. Sci.* 82:689–693 (1985). Eucaryotic expression vectors useful in producing variants of this invention may also contain inducible promoters or comprise inducible expression systems as are known in the art.

Established cell lines, including transformed cell lines, are suitable as hosts. Normal diploid cells, cell strains derived from in vitro culture of primary tissue, as well as primary explants (including relatively undifferentiated cells such as haematopoetic stem cells) are also suitable. Candidate cells need not be genotypically deficient in the selection gene so long as the selection gene is dominantly acting.

The host cells preferably will be established mammalian cell lines. For stable integration of the vector DNA into chromosomal DNA, and for subsequent amplification of the integrated vector DNA, both by conventional methods, CHO (Chinese Hamster Ovary) cells are presently preferred. Alternatively, the vector DNA may include all or part of the bovine papilloma virus genome (Lusky et al., *Cell*, 36: 391–401 (1984) and be carried in cell lines such as C127 mouse cells as a stable episomal element. Other usable mammalian cell lines include HeLa, COS-1 monkey cells, melanoma cell lines such as Bowes cells, mouse L-929 cells, 3T3 lines derived from Swiss, Balb-c or NIH mice, BHK or HaK hamster cell lines and the like.

Stable transformants then are screened for expression of the procoagulant product by standard immunological or activity assays. The presence of the DNA encoding the procoagulant proteins may be detected by standard procedures such as Southern blotting. Transient expression of the procoagulant genes during the several days after introduction of the expression vector DNA into suitable host cells such as COS-1 monkey cells is measured without selection by activity or immunologic assay of the proteins in the culture medium.

This invention thus provides a method for producing the proteins described herein which entails producing an appropriately engineered host cell, whether by transfection or transformation and culturing such transfected or transformed cells or their progeny to produce additional such cells, and then culturing the cells so provided under conditions permitting production of the protein. Suitable conditions include growth in conventional media supplemented with mammalian serum, e.g. up to 10% serum (vol/vol), or as described in WO 88/08035. The production media may optionally contain a protease inhibitor such as aprotinin, e.g., in an amount from about 0.1 to about 5%, preferably about 0.5 to about 1% (vol aprotinin solution/vol media) using an aprotinin solution containing 15–30 Trypsin inhibitor units (TIU) per ml of solution (Sigma), or corresponding amounts of activity units of other protease inhibitors.

Following the expression of the DNA by conventional means, the variants so produced may be recovered, purified, and/or characterized with respect to physiochemical, biochemical and/or clinical parameters, all by known methods.

Wild-type full length fVIII:c produced in mammalian host cells is characterized by an N-terminal heavy chain of ~200 kD and a C-terminal light chain of ~80 kD together with ~90 kD, ~73 kD and ~71 kD fragments. Upon treatment with thrombin, polypeptide fragments including the following are observed by SDS-PAGE: ~180 kD (smear), ~73 kD, ~65 kD (following digestion with factor Xa), ~54 kD, ~45 kD, and ~43 kD. The active species is believed to be a complex of the ~54 kD and ~90 kD polypeptides, perhaps in further association with the ~43 kD polypeptide. In the case of deletion analogs wherein the deletion is between the 90 kD and 80 kD sites, a single chain polypeptide may be observed with a molecular weight of up to ~200 kD, as well as a heavy chain of up to about ~180 kD and a light chain of ~80 kD. After thrombin digestion, a truncated B-domain may be observed of up to ~92 kD, as well as polypeptides of ~69, ~65 (after Xa digestion), ~50, ~45 & ~43 kD.

Expression in mammalian host cells of fVIII-encoding DNA sequences mutagenized to partially or completely abolish specific proteolysis at one or more cleavage sites in the protein as disclosed herein thus provides for the first time active procoagulant compositions comprising polypeptides characterized respectively by the following:

(a) the substantial absence of a ~80 kD polypeptide prior and subsequent to thrombin treatment, in embodiments wherein the peptide sequence is modified to prevent cleavage at the 80 kD site;

(b) the substantial absence of a ~65 kD fragment prior and subsequent to factor Xa treatment in embodiments wherein the peptide sequence is modified to prevent cleavage at the Xa site (at arg-1721);

(c) the substantial absence of a ~90 kD fragment prior and subsequent to thrombin treatment in embodiments wherein the peptide sequence is modified to prevent cleavage at the 90 kD site (at arg-740);

(d) the substantial absence of a ~44 kD fragment prior and subsequent to thrombin treatment in embodiments wherein the peptide sequence is modified to prevent cleavage at the APC site (at arg-336); and (e) combinations of (a) through (d) in embodiments wherein specific proteolysis at more than one of the cleavage sites is prevented.

The proteins of this invention have been found to bind to monoclonal antibodies directed to human Factor VIII:C and may thus be recovered and/or purified by immunoaffinity chromatography using such antibodies and/or by conventional protein purification methods applicable to Factor VIII. Furthermore, compounds of this invention have been found to possess procoagulant activity as measured by conventional clotting assays.

The compounds of this invention can be formulated into phararmaceutically acceptable preparations with a parenterally or otherwise acceptable vehicle and/or one or more excipients in accordance with procedures known in the art.

The pharmaceutical preparations of this invention, preferably suitable for parenteral administration, may conveniently comprise a sterile lyophilized preparation of the protein which may be reconstituted by addition of sterile solution to produce solutions preferably isotonic with the blood of the recipient. The preparation may be presented in unit or multi-dose containers, e.g. in sealed ampoules or vials. Their use would be analogous to that of human factor VIII, appropriately adjusted for potency.

Thus, pharmaceutical compositions of this invention may be administered to patients as a method for treating or preventing bleeding disorders, including Hemophilia A.

The invention will be further understood with reference to the following illustrative experimental examples and procedures, which are purely exemplary, and should not be taken as limiting the true scope of the present invention, as described in the claims.

PLASMID DERIVATIONS

The mutagenesis of fVIII cDNAs was performed directly in the expression plasmid in order to minimize effort in shuffling sequences between different vectors. Generally, the approach taken for mutagenesis was derived from the procedure of Morinaga with modifications. This approach is facilitated by the construction of plasmids which have convenient unique restriction sites in the fVIII expression plasmid. The following depicts the construction of a fVIII expression plasmid which has unique Eco RV, HpaI, Cla I and Xba I restriction sites. Plasmid pMT2 may be obtained by EcoRI digestion of pMT2-VWF, which has been deposited with the American Type Culture Collection under accession number ATCC 67122. EcoRI digestion excises the cDNA insert present in pMT2-VWF, yielding pMT2 in linear form which can be ligated and used to transform E. coli HB 101 or DH-5 to ampicillin resistance. Plasmid pMT2 DNA can be prepared by conventional methods. pMT2VIII was then constructed by digesting pMT2 with Eco RV and XbaI, treating the digested DNA with Klenow fragment of DNA polymerase I, and ligating Cla linkers (NEBiolabs, CATCGATG). This removes bases 2171 to 2421 starting from the Hind III site near the SV40 origin of replication and enhancer sequences of pMT2 (the ClaI derivative of pMT2). The factor VIII cDNA was exised from pSP64 VIII with SalI and blunted with T4 DNA polymerase, and EcoRI adapters were added (AATTCCTCGAGAGCT). The EcoRI-adapted factor VIII cDNA was then ligated into the EcoRI site of the ClaI derivative of pMT2. The resultant plasmid is called pMT2-VIII.

When the full length factor VIII expression plasmid is introduced into COS-1 cells, low levels of factor VIII are obtained. By deletion of a middle region of the factor VIII coding region (See related PCT application, supra) higher levels of FVIII activity were obtained which had biological characteristics very similar to the native forms of fVIII including thrombin activatibility. Thus, the analysis of mutations in fVIII cleavage sites was facilitated by studying the mutations in these deleted derivatives which are expressed more efficiently. Accordingly, pMT2-DGR, a deleted form of the fVIII expression plasmid pMT2VIII, was constructed by taking the KpnI (at 1961 in the fVIII cDNA) to the XbaI site (in the fVIII cDNA at 7096 base pairs) from pDGR-2 and ligating it into the KpnI-XbaI fragment of pMT2VIII.

MUTAGENESIS

The mutagenesis of specific sites in the factor VIII expression plasmid involves the following steps:

1) The plasmid pMT-DGR was linearized with ClaI, treated with calf intestine phosphatase, and separated on a 0.8% low melting temperature tris-acetate agarose gel. The linearized band was then extracted by adsorption to silica dioxide and eluted in tris-EDTA.

2) A second lot of pMT-DGR was digested with KpnI and XhoI or KpnI and XbaI as indicated below, and separated on a 0.8% low melting temperature agarose gel and extracted as above.

3) 1 ug of each of these plasmids were mixed, the volume adjusted to 18 ul, and 2.0 ul of 2N NaOH was added.

4) The mixture was denatured at room temperature for 10 min, then neutralized with 180 ul of a solution which is 0.02N HCl and 0.1M Tris-HCl pH 8.0.

5) 20 picomoles of phosphorylated mutagenic oligonucleotide was added to 40 ul of the heteroduplex mixture.

6) The mixture was placed in a 68° C. heat block for 90 min. After the incubation the mixture was allowed to slowly cool at room temperature.

7) For each mutagenic reaction, 40 ul of the heteroduplex oligonucleotide mixture was used. The reactions were made 2 mMMgCl$_2$, 1 mM beta-mercaptoethanol, 400 uM ATP, 100 uM deoxynucleotide triphosphate, 3–4 units/ul of Klenow fragment of *E. coli* DNA polymerase I and 400 units/ul of T4 DNA ligase.

8) The reactions were incubated for 10 minutes at room temperature, transferred to 16° C. and incubated overnight.

9) The reaction was terminated by phenol-chloroform extraction and ethanol precipitation, and the resultant pellet was washed with 70% ethanol and resuspended in 10 ul of sterile H$_2$O.

10) DNA was then used to transform competent HB101 or DH-5 bacteria. The ampicillin resistant colonies were screened with 1 × 10$^6$ cpm/ml of a $^{32}$P-labeled screening oligonucleotide in 5×SSC, 0.1% SDS, 5×denhardt's reagent, and 100 ug/ml denatured salmon sperm DNA.

11) The filters were washed with 5×SSC, 0.1% SDS at a temperature 5 degrees below the calculated melting temperature of the oligonucleotide probe.

12) DNA was prepared from positively hybridizing clones and analyzed initially by digestion with different restriction enzymes and agarose gel electrophoresis. DNA was transferred to nitrocellulose and filters were prepared and hybridized to the screening probes to ensure that the mutagenic oligonucleotide was introduced into the correct fragment.

13) DNA was then retransformed into *E. coli* and ampicillin resistant colonies were screened for hybridization to the screening oligonucleotide.

14) Final mutations were confirmed by DNA sequencing (Sanger et al., 1977, Proc. Natl. Acad. Sci. USA 74:5463–5467).

EXAMPLE 1

Alteration of the 80 kD Cleavage Site

The alteration of specific cleavage sites may be accomplished by changing the basic amino acid on the amino terminal side of a potential cleavage site. Since the choice of amino acid replacement can affect protein folding and/or function the best choices in this regard are conservative alterations. Some proteases, for example thrombin, are very specific for arginine. Thus, alteration of arginine to a lysine may significantly inhibit cleavage. More dramatic modification, for example a change to isoleucine, would guarantee resistance to proteolysis. Since the protease involved in the cleavage of the 80 kD is not known, a change from the arginine at position 1648 to an isoleucine was performed. The mutagenic oligonucleotide was the 39-mer, No. 1 of Table III. The screening nucleotide was the 15-mer, No. 2 of Table III. The mutagenesis was carried out as above with the KpnI-XbaI fragment of pMT2-DGR and the ClaI digested linear form of pMT2-DGR. The resultant mutant was demonstrated to be correct by DNA sequencing (Sanger et al., supra). DNA (pCSM 1648) was prepared by banding in CsCl and used to transfect COS-1 monkey cells as described (Kaufman, PNAS, 1985, 82:689). 60 hr. post transfection, samples of the conditioned media were taken for factor VIII activity assay by the Kabi Coatest chromagenic assay method (Kabi) or the ability to clot factor VIII deficient plasma (Activated Partial Thromboblastin Time, APTT) before and after thrombin activation. Results from the activity assays are shown in Table IV. The mutation of the 80 cleavage site did not decrease the activity of factor VIII generated in the conditioned media. In addition, there was no change in the thrombin activation coefficient. In order to demonstrate that the mutation did actually destroy the cleavage site, the transfected cells were labeled with $^{35}$S-methionine for 6 hrs and conditioned media and cell extracts prepared for analysis by immunoprecipitation and SDS-polyacrylamide gel electrophoresis. The results demonstrated that the alteration of Arg to Ile did not affect the synthesis or secretion of the factor VIII variant from the cell. Analysis of the radiolabeled protein after thrombin digestion indicated a normal appearance of the 73 kD, and 54 and 44 kd fragments. However, the predominant factor VIII species produced was a single chain molecule as a result of resistance to cleavage at the 80 kD site. This result demonstrated that single chain factor VIII is as active as the native molecule. The single-chain Factor VIII:c variants may be advantageous in that they may be produced in more homogeneous form and may have an improved pharmacokinetic profile relative to natural human or other recombinant Factor VIII:c proteins.

EXAMPLE 2

An alternative to the arg→ile change at the 80 kD cleavage site was to introduce an N-linked glycosylation site at asparagine adjacent to the arg in order to attempt to block cleavage. The potential advantage of this alteration is that the resultant protein would have a carbohydrate moiety to potentially block the modified amino acid from provoking an immunologic response. Thus mutagenic oligonucleotide No. 3 of Table III was synthesized. This mutagenesis event converted a Gln-Arg-Glu-Ile-Thr sequence to Gln-Arg-Asn-Ile-Thr. The oligonucleotide used for screening for the mutation was the 14-mer. No. 4 of Table III. For this mutation, the mutagenesis was done in the native, not deleted, factor VIII cDNA which was cloned into a single stranded phage M13 vector. The SalI fragment containing the entire factor VIII cDNA was inserted into the Xho I site of the M13 origin vector, pGC2. pGC2 is a plasmid containing ampicillin resistance, an *E. coli* origin of replication, an M13 origin of replication and a polylinker containing a XhoI site. Other similar, commercially available plasmids may also be used, of course. The phosphorylated (20 pMoles) mutagenic oligonucleotide was annealed in 10 ul with 1 ug of template containing 20 mM Tris-HCl, 10 mM MgCl$_2$, 50 mM NaCl, 1 mM dithiothreitol, at 65° C. for 10 min. The reaction was slowly cooled and 10 ul of solution B [20 mM Tris-HCl pH 7.5, 10 mM MgCl$_2$, 10 mM dithiothreitol, 1 mM of each nucleotide triphosphate (dATP, dGTP, dCTP, and dTTP), 10 mM ATP, 400 units/ml ligase and 3–4 units/ul of Klenow fragment of DNA polymerase I], incubated 5 min at 23° C. and then incubated overnight at 16° C. The reaction was terminated by phenol-chloroform extraction and ethanol precipitation. The DNA was resuspended in 10 ul of 10 mM Tris-HCl pH 7.5 and 1 mM EDTA, and 1 ul taken to transform *E. coli*. HB101.

DNA (CSM-1649) was prepared and transfected into COS-1 cells as above. After transfection of COS-1 cells as before the conditioned media was assayed and found to contain a relatively low level of activity similar to that produced by the wild-type Factor VIII:c cDNA in pMT2. Analysis of $^{35}$S-methionine labeled protein as above indicated that the addition of the N-linked sugar partially blocked cleavage. The ability of this particular type of mutation to block cleavage and allow secretion will probably vary from one protein sequence to another depending on the structure of the protein.

EXAMPLE 3

Mutation of the 90 kD Cleavage Site

The mutation of the arginine to an isoleucine at position 740 was performed with oligonucleotide No. 5 of Table III. The correct mutations were screened with 15-met No. 6 of Table III. The mutagenesis was performed with the KpnI-XbaI fragment of pMT2-DGR and the ClaI-digested linear form of pMT2-DGR. The resulting DNA (CSM-740) was prepared and transfected as described above. Samples were assayed as described above and CSM-740 was found to generate less activity than pMT2-DGR. Analysis of $^{35}$S-methionine labeled cell extracts and conditioned media by immunoprecipitation and gel electrophoresis indicated that Factor VIII synthesis, secretion, activity, and thrombin activation were not dramatically modified by alteration of this cleavage site. Close inspection indicated a less efficient level of secretion for CSM-740. Thus, cleavage of the 90 kD cleavage site is not essential for factor VIII activity.

EXAMPLE 4

Mutation of the Thrombin Cleavage Site at 372

A. The mutagenic oligonucleotide to convert an arginine to an isoleucine at position 372 was oligonucleotide No. 7 of Table II. The oligonucleotide used to identify correct mutations was No. 8 of Table III. The mutagenesis was carried out with the KpnI-XhoI fragment of pMT2-DGR and the ClaI digested linear form of pMT2-DGR. The resultant plasmid DNA (CSM-372) was prepared and transfected into COS-1 cells as described above. Samples were assayed as above. The results demonstrated that destruction of the 372 cleavage site results in a loss of more than 90% of factor VIII activity. In addition, thrombin treatment does not restore activity. Further analysis indicated that the modified form of factor VIII was properly synthesized and secreted.

B. To produce the K-372 variant, Example 4A may be repeated using analogs of oligonucleotides 7 and 8 of Table III which contain a Lys codon, e.g. AAA, instead of the Ile codon ATC.

EXAMPLE 5

Mutation of the Thrombin Cleavage Site at R-336 (The Proposed Activated Protein C Cleavage Site)

A. The mutagenic oligonucleotide to convert an arginine to a lysine at position 336 was oligonucleotide No. 9 of Table III. The oligonucleotide used to screen the mutations was No. 10. The mutagenesis was carried out with the KpnI-XhoI fragment of pMT2-DGR and the ClaI digested linear form of pMT2-DGR. The resultant DNA (CSM-336) was prepared, transfected, and resultant samples assayed as above. The results indicate increased activity and a normal thrombin activatibility. The modified factor VIII was not affected in its synthesis or secretion. The increased activity may be attributable to loss of inactivation as a result of proposed Xa cleavage in the cobas assay. Thus, this alteration appears to generate a more stable form of fVIII.

B. To produce the I-336 variant Example 5A was repeated using analogs of oligonucleotides 9 and 10 of Table II which contain an Ile codon, e.g. ATC, instead of the Lys codon AAG. The I-336 variant so produced had similar biological properties to those of the K-336 variant. Additionally, full-length I-336 and K-336 variants were produced and found to possess similar biological properties to those of the corresponding mutant deletion variants.

EXAMPLE 6

Mutation of the 73 kD Cleavage Site

A. The oligonucleotide for mutagenesis of the arginine to a lysine was No. 11 of Table III. The screening oligonucleotide was the 15-mer No. 12 of Table III. Mutagenesis was performed with the KpnI-XbaI fragment of pMT2-DGR and the ClaI digested linear form of pMT2-DGR. DNA harboring the correct mutation (CSM-1689) was prepared and transfected into COS cells. Cells were analyzed as above. Results indicate that mutation of the 73 kD cleavage site results in similar activity to that generated by pMT2-DGR. Thus, our lysine-for-arginine mutation at the 73 kD cleavage site does not destroy Factor VIII:c activity.

B. To produce the I-1689 variant Example 6A was repeated using analogs of oligonucleotides 11 and 12 of Table III which contain an Ile codon, e.g. ATC, instead of the Lys codon AAA. Surprisingly, the I-1689 variant so produced was found to possess less than 90% of the Factor VIII:c activity obtained with pMT2-DGR. Our results suggest that cleavage at the 73 kD site is important in activating the molecule and that substitution of Lys for Arg-1689 does not abolish such cleavage. Furthermore, K-1689 variants may be useful therapeutically, perhaps with delayed onset of Factor VIII:c activity.

EXAMPLE 7

Preparation of Other FVIII Variants

Vectors encoding full length or deleted FVIII were modified to encode the proteins listed in Table V. In cases involving multiple modifications, the starting vector, either pMT2-DGR, pMT2pc-DGR, pMT2-LA or pMT2-VIII, was mutagenized iteratively using appropriate oligonucleotides and previously described methods to effect all of the desired mutagenesis events. The resultant vector, correctly mutagenized, was transfected into COS cells and the variant so produced was studied, as previously described. The results, indicating substantial retention of procoagulant activity are shown in Tables V and VI.

Although the majority of these mutations were constructed and analyzed in deleted forms of factor VIII (DGR and 90-80), the alterations can be made directly with DNA encoding full-length factor VIII or can be reintroduced from mutagenized deletion variant DNA into the full length factor VIII cDNA by digestion of mutagenized deletion variant DNA and DNA encoding w.t. Factor VIII:c with the appropriate enzymes and ligation of the appropriate fragments to generate the desired plasmids. In addition, a similar approach can be used to introduce multiple mutations into the factor VIII cDNA. In every case tested we have found that results obtained with mutagenized deletion variants were also obtained with the corresponding full-length variants and that the effect of making multiple amino acid substitutions may be additive with respect to the separately observed results for particular amino acid modifications. Furthermore, all variants expressed in CHO cells and subsequently tested yielded assay results similar to the COS-produced variants. Variants containing amino acid modification at both the proposed APC cleavage site, e.g. at R-336, and the Xa cleavage site at R-1721 should be particularly stable variants that are resistant to inactivation.

TABLE IV

Activity of modified forms of factor VIII expressed in COS-1 cells:

| Mutation | Activity mU/ml | Thrombin Activation |
|---|---|---|
| Experiment 1 | | |
| CSM-336 R → K | 431 | 10-fold |
| CSM-372 R → I | 10 | — |
| CSM-740 R → I | 114 | 10-fold |
| CSM-1648 R → I | 246 | 10-fold |
| CSM-1721 R → I | — | |
| CSM-336, 1721 | | |
| pMT2-DGR | 288 | 10-fold |
| Experiment 2 | | |
| CSM-1649 E → N | 196 | 10-fold |
| pMT2VIII | 185 | 10-fold |
| Experiment 3 | | |
| CSM-1689 R → K | 88 | N.T. |
| pMT2-DGR | 103 | N.T. |
| Experiment 4 | | |
| p90-80/336 R → I | — | |
| p90-80 | — | |

N.T. = Not Tested

TABLE V

Activity of COS-produced Variants

| variant[1] | 63 hrs (21 hrs) | ave | 87 hrs[2] (45 hrs) | ave post tfx (postfeed) |
|---|---|---|---|---|
| mock | — | — | — | — |
|  | — | — | — | — |
| VIII (wt) | 99 | 102 | 111 | 118 |
|  | 105 | | 125 | |
| DGR-226 | 85 | 89 | 128 | 125 |
|  | 92 | | 122 | |
| VIII-336 | 135 | 154 | 180 | 180 |
|  | 172 | | 179 | |
| VIII-562 | 67 | 72 | 89 | 90 |
|  | 78 | | 91 | |
| VIII-1313 | 106 | 116 | 147 | 147 |
|  | 126 | | 146 | |
| VIII-1313, 1648 | 115 | 134 | 178 | 184 |
|  | 152 | | 190 | |
| VIII-226, 336, 562 | 65 | 70 | 81 | 78 |
|  | 74 | | 74 | |
| VIII-336, 1313, 1648 | 149 | 145 | 192 | 188 |
|  | 140 | | 184 | |
| VIII-336, 740, 1313, 1640, 1721 | 89 | 77 | 101 | 98 |
|  | 64 | | 95 | |
| LA (pMT2) | 79 | 71 | 90 | 91 |
|  | 63 | | 91 | |
| LA (pMT2pc) | 69 | 65 | 109 | 99 |
|  | 60 | | 88 | |

[1]Variants are indicated by naming the pearent compounds (FVIII, DGR or LA, as previously described) followed by specification of which arginines were converted to isoleucines;
[2]this time point is for conditioned media which had been spun to remove cells
NB-One P100 plate of each sample was 35S-methionine steady state labeled

TABLE VI

Summary of Additional FVIII COBAS Assays hrs post transfection:

| variant[1]: | 38.5 (−.5)[2] | 48 (9) | 63 (24) | 72 (33) | 85 (46) |
|---|---|---|---|---|---|
| mock | 0 | 0 | 0 | 0 | 0 |

TABLE VI-continued

Summary of Additional FVIII COBAS Assays hrs post transfection:

| variant[1]: | 38.5 (−.5)[2] | 48 (9) | 63 (24) | 72 (33) | 85 (46) |
|---|---|---|---|---|---|
| DGR | 49 | 83 | 136 | 212 | 338 |
| DGR-226 | 36 | 66 | 105 | 164 | 210 |
| DGR-336 | 78 | 90 | 192 | 295 | 400 |
| DGR-1721 | 48 | 83 | 173 | 206 | 294 |
| DGR-226 & 336 | 64 | 97 | 209 | 235 | 306 |
| DGR-226, 336 & 1721 | 41 | 57 | 142 | 165 | 241 |
| FVIII (wt) | 31 | 54 | 137 | 163 | 214 |
| VIII-562 | 19 | 37 | 72 | 77 | 119 |
| VIII-1313 | 30 | 49 | 111 | 145 | 178 |
| VIII-1648 | 35 | 57 | 123 | 155 | 204 |
| VIII-1313, 1648 & 1721 | 29 | 49 | 98 | 124 | 154 |
| VIII-226, 336 & 562 | 20 | 33 | 69 | 92 | 88 |

[1]variants are named as on Table IV;
[2]times in parentheses are times measured from media change (feed)

What is claimed is:

1. An isolated protein having procoagulant activity in a conventional clotting assay and an amino acid sequence substantially that of human factor VIII:c, wherein one to three amine acids selected from the group consisting of:
   (a) the arginine at one or more of positions 220, 250, 279, 282, 359, 698, 700, and 1719;
   (b) one or both lysines at positions 325 and 338;
   (c) one or more tyrosines at positions 346, 395, 407, 1664 and 1680, and
   (d) serine at position 741 is deleted or replaced with an independently selected replacement amino acid, wherein said positions for replacement or deletion of amino acids are chosen with reference to FIGS. 1A and 1B.

2. The protein of claim 1, further characterized in that a tripeptide sequence encompassing one or more of positions 220, 250, 279, 282, 325, 338, 359, 741, or 1719 is replaced with a tripeptide sequence comprising Asn-X-Thr or Asn-X-Ser, wherein X is any amino acid.

3. The protein of claim 2, wherein X is not Arg.

4. An isolated protein having procoagulant activity in a conventional clotting assay and an amino acid sequence substantially that of human Factor VIII:c, wherein one to three amino acids selected from the group consisting of:
   (a) the arginine at one or more of positions 220, 250, 279, 282, 359, 698, 700, and 1719;
   (b) one or both lysines at positions 325 and 338;
   (c) one or more tyrosines at positions 346, 395, 407, 1664 and 1680, and
   (d) serine at position 741 is deleted or replaced with an independently selected replacement amino acid; and wherein said protein is further characterized by deletion of amino acids from A-982 through L-1562, wherein said positions for replacement or deletion of amino acids are chosen with reference to FIGS. 1A and 1B.

5. An isolated protein having procoagulant activity in a conventional clotting assay and an amino acid sequence substantially that of human Factor VIII:c, wherein one to three amino acids selected from the group consisting of:
   (a) the arginine at one or more of positions 220, 250, 279, 292, 359, 698, 700, and 1719;

(b) one or both lysines at positions 325 and 338;
(c) one or more tyrosines at positions 346, 395, 407, 1664 and 1680, and
(d) serine at position 741 is deleted or replaced with an independently selected replacement amino acid; and wherein said protein is further characterized by deletion of amino acids from T-760 through N-1639, wherein said positions for replacement or deletion of amino acids are chosen with reference to FIGS. 1A and 1B.

6. An isolated protein having procoagulant activity in a conventional clotting assay and an amino acid sequence substantially that of human Factor VIII:c, wherein one to three amino acids selected from the group consisting of:
   (a) the arginine at one or more of positions 220, 250, 279, 282, 359. 698, 700, and 1719;
   (b) one or both lysines at positions 325 and 338;
   (c) one or more tyrosines at positions 346, 395, 407, 1664 and 1680, and
   (d) serine at position 741 is deleted or replaced with an independently selected replacement amino acid; and wherein said protein is further characterized by deletion of amino acids from S-741 through R-1648, wherein said positions for replacement or deletion of amino acids are chosen with reference to FIGS. 1A and 1B.

7. An isolated cDNA encoding the protein of claim 1.

8. A host cell containing a cDNA of claim 7 operably linked to an expression control sequence and capable of expressing the protein encoded by the cDNA.

9. A method for producing a protein having procoagulant activity and an amino acid sequence substantially that of human factor VIII:c characterized in that one to three amino acids selected from the group consisting of:
   (a) the arginine at one or more of positions 220, 250, 279, 282, 359, 698, 700, and 1719;
   (b) one or both lysines at positions 325 and 338;
   (c) one or more tyrosines at positions 346, 395, 407, 1664 and 1680; and, .
   (d) serine at position 741; is deleted or replaced with an independently selected replacement amino acid, wherein said positions for replacement or deletion of amino acids are chosen with reference to FIGS. 1A and 1B, said method comprising:
   (i) producing a host cell of claim 8, and
   (ii) culturing the host cell or the progeny thereof under conditions permitting production of the protein.

10. An isolated cDNA encoding the protein of claim 4.

11. A host cell containing a cDNA of claim 4 operably linked to an expression control sequence and capable of expressing the protein encoded by the cDNA.

12. An isolated cDNA encoding the protein of claim 5.

13. A host cell containing a cDNA of claim 5 operably linked to an expression control sequence and capable of expressing the protein encoded by the cDNA.

14. An isolated cDNA encoding the protein of claim 6.

15. A host cell containing a cDNA of claim 6 operably linked to an expression control sequence and capable of expressing the protein encoded by the cDNA.

16. A method for producing a protein selected from the group consisting of a protein of claim 4, 5, and 6, comprising the steps of:
   (i) producing a host cell selected from the group consisting of a host cell of claim 11, 13, and 15, and
   (ii) culturing said host cell or the progeny thereof under conditions permitting production of said protein.

17. A pharmaceutical composition for treating or preventing bleeding disorder symptoms which comprises a procoagulant-effective amount of a protein of claim 1 in admixture with a pharmaceutically acceptable vehicle.

18. A pharmaceutical composition for treating or preventing bleeding disorder symptoms which comprises a procoagulant-effective amount of a protein of claim 2 in admixture with a pharmaceutically acceptable vehicle.

19. A pharmaceutical composition for treating or preventing bleeding disorder symptoms which comprises a procoagulant-effective amount of a protein of claim 4 in admixture with a pharmaceutically acceptable vehicle.

20. A pharmaceutical composition for treating or preventing bleeding disorder symptoms which comprises a procoagulant-effective amount of a protein of claim 5 in admixture with a pharmaceutically acceptable vehicle.

21. A pharmaceutical composition for treating or preventing bleeding disorder symptoms which comprises a procoagulant-effective amount of a protein of claim 6 in admixture with a pharmaceutically acceptable vehicle.

* * * * *

UNITED STATES PATENT AND TRADEMARK OFFICE
CERTIFICATE OF CORRECTION

PATENT NO. : 5,422,260

DATED : June 6, 1995

INVENTOR(S) : Randal J. Kaufman, *et al.*

Page 1 of 3

It is certified that error appears in the above-indentified patent and that said Letters Patent is hereby corrected as shown below:

At column 2, line 19      please replace "a priori" with --*a priori*--.

At column 4, line 10      please replace "in vivo" with --*in vivo*--.

At columns 5/6, second line after the heading in Table I      please replace "TRRYYLGAV" with --TRRYYLGAVE--.

At column 6, last line      the last line of numbers (*i.e.*, 1540) should not be separated from the first line of characters (*i.e.*, KPDLPKTSGK . . .) at columns 7 and 8. The numbers and characters should stay together on one page.

At columns 7 and 8, Table I, line 3      please replace "QKDLEPTETS" with --QKDLFPTETS--.

At columns 7 and 8, Table I, line 4      please replace "LDPLSWDNHY" with --LDPLAWDNHY--.

At columns 7 and 8, Table I, line 5      please replace "VLKRHQRETT" with --VLKRHQREIT--.

At column 8, line 55      please delete the words "Pat. No.".

At column 9, line 13      please underline the words "kD", "kD" and "Xa", respectively.

UNITED STATES PATENT AND TRADEMARK OFFICE
CERTIFICATE OF CORRECTION

PATENT NO. : 5,422,260
DATED : June 6, 1995
INVENTOR(S) : Randal J. Kaufman, et al.

It is certified that error appears in the above-indentified patent and that said Letters Patent is hereby corrected as shown below:

At column 9, line 14      please delete the underline under the words "R &/or R".

At column 9, line 58,      for Compound 53, please delete the "X" under the column labeled "1721", and place an additional "X" under the columns labeled "740" and "1719" respectively.

At column 10, line 45      please replace "supra" with --*supra*--.

At column 11, line 12      please replace "inter alia" with --*inter alia*--.

At column 13, line 42      please replace "in vitro" with --*in vitro*--.

At column 15, line 41      please replace "pharamaceutically" with --pharmaceutically--.

At column 16, line 34      please replace "supra" with --*supra*--.

At column 17, line 6      please replace "2 mMMgCl$_2$," with --2mM MgCl$_2$,--.

At column 19, line 15      please replace "15-met" with --15-mer--.

At column 19, lines 51 and 52      please replace "AAA" with --AAA-- and "ATC" with --ATC--.

At column 20, lines 5 and 6      please replace "ATC" with --ATC-- and "AAG" with --AAG--.

At column 20, lines 30 and 31      please replace "ATC" with --ATC-- and "AAA" with --AAA--.

UNITED STATES PATENT AND TRADEMARK OFFICE
CERTIFICATE OF CORRECTION

PATENT NO. : 5,422,260

DATED : June 6, 1995

INVENTOR(S) : Randal J. Kaufman, et al.

It is certified that error appears in the above-indentified patent and that said Letters Patent is hereby corrected as shown below:

At column 21, line 57      please replace "pearent" with --parent--.

At column 22, line 20      please replace "Table IV" with --Table V--.

At column 22, line 27, please replace "amine" with --amino--.

At column 22, line 68, please replace "292," with --282,--.

At column 23, line 17, please replace "359." with --359,--.

Signed and Sealed this

Twentieth Day of February, 1996

Attest:

Bruce Lehman

BRUCE LEHMAN

Attesting Officer      Commissioner of Patents and Trademarks